US008119779B2

(12) United States Patent
McGuigan et al.

(10) Patent No.: US 8,119,779 B2
(45) Date of Patent: Feb. 21, 2012

(54) PHOSPHORAMIDATE DERIVATIVES

(75) Inventors: Christopher McGuigan, Cardiff (GB); Antonella Carangio, Verona (IT); Bruce Caterson, Cardiff (GB); Clare Elizabeth Hughes, Cardiff (GB); Clare Louise Curtis, Stroud (GB)

(73) Assignee: University College Cardiff Consultants Limited

( * ) Notice: Subject to any disclaimer, the term of this patent is extended or adjusted under 35 U.S.C. 154(b) by 1302 days.

(21) Appl. No.: 10/586,101

(22) PCT Filed: Jan. 18, 2005

(86) PCT No.: PCT/GB2005/000161
§ 371 (c)(1),
(2), (4) Date: May 29, 2007

(87) PCT Pub. No.: WO2005/070944
PCT Pub. Date: Aug. 4, 2005

(65) Prior Publication Data
US 2007/0275910 A1    Nov. 29, 2007

(30) Foreign Application Priority Data
Jan. 19, 2004  (GB) .................................. 0401088.0

(51) Int. Cl.
C07H 5/04 (2006.01)
C07H 5/06 (2006.01)
C07H 1/00 (2006.01)
C07H 3/00 (2006.01)
C08B 37/00 (2006.01)

(52) U.S. Cl. ...................................... 536/18.7; 536/124
(58) Field of Classification Search .................. None
See application file for complete search history.

(56) References Cited

U.S. PATENT DOCUMENTS
2002/0045597 A1   4/2002  Anastassiades et al.

FOREIGN PATENT DOCUMENTS
| EP | 0482206 | 4/1992 |
| JP | 2001220397 | 8/2001 |
| WO | WO 97/48399 | 12/1997 |
| WO | WO 97/48400 | 12/1997 |
| WO | WO 99/37753 | 7/1999 |
| WO | WO 00/00501 | 1/2000 |
| WO | WO 00/18775 | 4/2000 |
| WO | WO 00/47591 | 8/2000 |
| WO | WO 2005/070944 | 8/2005 |

OTHER PUBLICATIONS

McGuigan et al., "Phosphate Prodrugs Derived from N-Acetylglucosamine Have Enhanced Chondroprotective Activity in Explant Cultures and Represent a New Lead in Antisteoarthritis Drug Discovery," J. Medicinal Chemistry, 51(18), 5807-5812 (2008): WEB publ. Aug. 21, 2008.*
International Search Report: PCT/GB2005/000161 filed Jan. 18, 2005, mailed Jun. 6, 2005.
International Preliminary Report on Patentability: PCT/GB2005/000161 filed Jan. 18, 2005, issued Jul. 24, 2005.
Written Opinion of the International Searching Authority: PCT/GB2005/000161 filed Jan. 18,2005.
Search Report for corresponding GB patent application No. 0401088.0, dated May 14, 2004.

* cited by examiner

Primary Examiner — Lawrence E Crane
(74) Attorney, Agent, or Firm — Fish & Richardson P.C.

(57) ABSTRACT

The present invention provides a phosphoramidate compound having the structure (I)

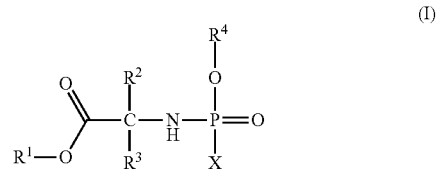

wherein X comprises a monosaccharide group comprising the structure (II) or (III)

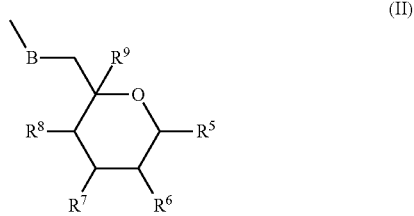

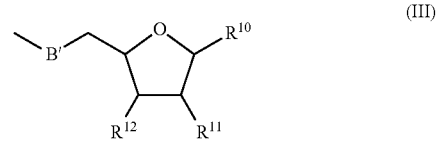

or a pharmaceutically acceptable salt, ester or salt of such ester. The present invention also provides processes for the production of (I) and uses thereof.

20 Claims, No Drawings

PHOSPHORAMIDATE DERIVATIVES

This application is a US national stage under 35 U.S.C. §371 of PCT/GB2005/000161 filed 18 Jan. 2005, which in turn claims priority to British application number 0401088.0 filed 19 Jan. 2004. These applications are herein incorporated by reference.

FIELD OF INVENTION

The invention relates to phosphoramidate derivatives, compositions thereof and processes for the manufacture thereof.

BACKGROUND OF INVENTION

Sugars are essential components for life, their analogues and derivatives forming the basis of numerous therapies, medicines and treatments.

Sugars are often polar, hydrophilic molecules, and tend to suffer from poor bioavailability and poor cell uptake by passive diffusion. Sugars may be subject to active transport into cells. However, this varies from cell type to cell type, and will be saturable at high concentrations.

A number of sugars undergo phosphorylation inside the cell in order to provide their desired function. This may be a rate-limiting step which limits the potency and availability of the sugar in biological systems.

Osteoarthritis affects more than one million people per annum in the UK. It is currently a poorly treated disease, with systemic treatments including NSAIDs, COX-2 inhibitors and other over-the-counter remedies. Surgery is a common treatment, but is disadvantageous as it is highly invasive, expensive, and of limited accessibility.

Glucosamine is widely used as an over-the-counter pharmaceutical composition for the prophylaxis and treatment of arthritis, most notably osteoarthritis.

It is desirable to provide an alternative and/or improved treatment for arthritis, preferably osteoarthritis.

SUMMARY OF INVENTION

According to a first aspect of the present invention, there is provided a phosphoramidate compound comprising the structure (I)

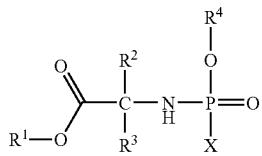

(I)

wherein:
X comprises a monosaccharide group comprising the structure (I) or (III)

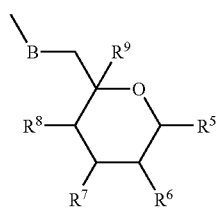

(II)

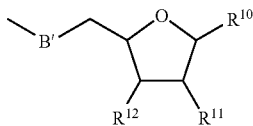

(III)

B and B' are independently selected from the group consisting of —O—, —CH$_2$— and a bond;

R$^1$ is selected from the group consisting of —H, protecting groups and monovalent hydrocarbon radicals;

R$^2$ and R$^3$ are independently selected from the group consisting of —H and monovalent hydrocarbon radicals, or R$^2$ and R$^3$ together form an alkylene or heteroalkylene chain so as to provide, together with the C atom to which they are attached, a cyclic system;

R$^4$ is selected from the group consisting of —H and monovalent hydrocarbon radicals;

R$^5$-R$^{12}$ are independently selected from the group consisting of —H, —OH, N$_3$, halogen, —SH, —OR$^{13}$, —SR$^{13'}$, NHR$^{14}$, —NR$^{14}_2$ and group

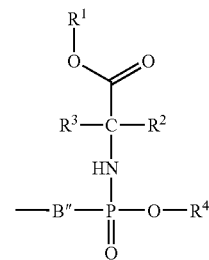

wherein B" is selected from the group consisting of —O—, —H$_2$— and a bond;

wherein R$^1$-R$^4$ are independently selected and are as defined above, wherein R$^{13}$ and R$^{13'}$ are independently selected from the group consisting of —H, monovalent hydrocarbon radicals, protecting groups and —C(O)R$^{15}$, and wherein R$^{14}$ is selected from the group consisting of —H monovalent hydrocarbon radicals, protecting groups and —C(O)R$^{15}$, wherein R$^{15}$ is selected from the group consisting of —H and monovalent hydrocarbon radicals;

or a pharmaceutically acceptable derivative or metabolite of a compound of formula (I).

B, B" and B'" are preferably —O—.

R$^1$ is preferably selected from the group consisting of —H, C$_{1-20}$ alkyl, C$_{2-20}$ alkenyl, C$_{2-20}$ alkynyl, C$_{3-30}$ cycloalkyl, C$_{3-30}$ cycloalkenyl, C$_{4-30}$ cycloalkynyl, C$_{7-30}$ aralkyl, C$_{7-30}$ alkaryl and C$_{5-30}$ aryl.

R$^1$ is more preferably selected from the group consisting of C$_{1-16}$ alkyl, C$_{2-16}$ alkenyl, C$_{2-16}$ alkynyl, C$_{3-20}$ cycloalkyl, C$_{3-20}$ cycloalkenyl, C$_{4-20}$ cycloalkynyl, C$_{7-20}$ aralkyl, C$_{7-20}$ alkaryl and C$_{6-20}$ aryl.

R$^1$ is more preferably selected from the group consisting of primary or secondary C$_{1-6}$ alkyl, C$_{2-6}$ alkenyl, C$_{5-7}$ cycloalkyl, C$_{5-7}$ cycloalkenyl, C$_{5-7}$ cycloalkynyl, C$_{5-11}$ ar-C$_{1-6}$ alkyl, C$_{1-6}$ alk-C$_{5-11}$ aryl and C$_{5-11}$ aryl.

Preferably, R$^1$ is selected from the group consisting of methyl, ethyl propyl, butyl, hexyl, cyclohexyl octyl, nonyl, dodecyl, eicosyl, norbornyl, adamantyl, vinyl, propenyl, cyclohexenyl, benzyl, phenylethyl, phenylpropyl, phenyl, tolyl, dimethylphenyl, trimethylphenyl, ethylphenyl, propylphenyl, biphenyl, naphthyl, methylnaphthyl, anthryl, phenanthryl, benzylphenyl, pyrenyl, acenaphthyl, phenalenyl, aceanthrylenyl, tetrahydronaphthyl, indanyl, biphenyl and structural isomers thereof, preferably methyl, ethyl, propyl and isopropyl.

Preferably, $R^1$ is selected from the group consisting of methyl, ethyl, 2-butyl, benzyl. Preferably $R^1$ is benzyl.

$R^2$ and $R^3$ are preferably independently selected from the group consisting of —H, $C_{1-20}$ alkyl, $C_{2-20}$ alkenyl, $C_{2-20}$ alkynyl, $C_{3-30}$ cycloalkyl, $C_{3-30}$ cycloalkenyl, $C_{4-30}$ cycloalkynyl, $C_{7-30}$ aralkyl, $C_{7-30}$ alkaryl, and $C_{5-30}$ aryl.

Preferably, at least one of $R^2$ and $R^3$ is selected from the group consisting of —H, primary, secondary and tertiary $C_{1-4}$ alkyl, $C_{5-7}$ ar-$C_{1-3}$ alkyl and $C_{1-3}$ alk-$C_{5-7}$ aryl, or, $R^2$ and $R^3$ together form an alkylene or heteroalkylene chain so as to provide, together with the C atom to which they are attached, a group selected from $C_{3-8}$ cycloalkyl, $C_{3-8}$ cycloalkenyl, and $C_{4-8}$ cycloalkynyl.

Preferably, at least one of $R^2$ and $R^3$ is selected from the group consisting of —H, methyl, propyl isopropyl, butyl, isobutyl, phenyl, hydroxyphenyl, indolyl, thiol, alkylthio, thioalkyl, hydroxyalkyl, amino, alkylimino, imino, alkyl-NH—, $H_2N$-alkyl-, imidazolyl, amido and carboxyl.

Preferably, $R^2$ and $R^3$ are independently selected from the group consisting of —H, methyl, benzyl, isopropyl, propyl, n-butyl, s-butyl, t-butyl, or, $R^2$ and $R^3$ together form an alkylene or heteroalkylene chain so as to provide, together with the C atom to which they are attached, a group selected from $C_3$— cycloalkyl, $C_{3-4}$ cycloalkenyl, and $C_{4-6}$ cycloalkynyl.

Preferably, $R^2$ is —H or methyl.

Preferably, both $R^2$ and $R^3$ are methyl.

Preferably, $R^2$ is —H and $R^3$ is methyl.

Preferably, both $R^2$ and $R^3$ together form a cyclopentyl ring.

Preferably, one or both of $R^2$ and $R^3$, either taken separately or together, corresponds to the side chains of any naturally occurring amino acid.

Preferably, the group —NH—$CR^2R^3$—$CO_2R^1$ is a —NH—$CHR^3$—$CO_2R^1$ group, which corresponds to a carboxy-protected α-amino acid.

Preferably, the group $R^3$ corresponds to the side chain of a naturally occurring amino acid such as Alanine, Arginine, Asparagine, Aspartic Acid, Cysteine, Cystine, Glycine, Glutamic Acid, Glutamine, Histidine, Isoleucine, Leucine, Lysine, Methionine, Phenylalanine, Serine, Threonine, Tryptophan, Tyrosine, Valine.

Preferably, when $R^2$ is H, the stereochemistry at the asymmetric centre —$CHR^3$— corresponds to an L-amino acid.

When $R^2$ and $R^3$ are different, all stereoisomeric forms of the asymmetric centre —$CR^2R^3$— are intended to fall within the scope of the present invention, i.e. both L and D stereoisomers.

$R^4$ is preferably selected from the group consisting of —H, $C_{1-20}$ alkyl, $C_{2-20}$ alkenyl, $C_{2-20}$ alkynyl, $C_{3-30}$ cycloalkyl, $C_{3-30}$ cycloalkenyl, $C_{4-30}$ cycloalkynyl, $C_{7-30}$ aralkyl, $C_{7-30}$ alkaryl and $C_{5-30}$ aryl.

$R^4$ is more preferably selected from the group consisting of $C_{1-15}$ alkyl, $C_{2-15}$ alkenyl, $C_{2-15}$ alkynyl, $C_{3-20}$ cycloalkyl, $C_{3-20}$ cycloalkenyl, $C_{4-20}$ cycloalkynyl, $C_{7-20}$ aralkyl, $C_{7-20}$ alkaryl and $C_{6-20}$ aryl.

$R^4$ is preferably substituted or unsubstituted $C_{7-12}$ alkaryl, substituted or unsubstituted $C_{7-12}$ aralkyl or substituted or unsubstituted $C_{6-12}$ aryl. Preferably, $R^4$ comprises alkaryl, aralkyl or aryl, substituted with one or more electron donating groups.

The term "electron-donating group", as used herein, means a functionality which draws electrons to itself less than a hydrogen atom would at the same position.

It has been found that where $R^4$ is phenyl or benzyl, in particular a phenyl or benzyl group substituted with an electron-donating group, the stability and/or the activity of the compound is increased.

Preferably, $R^4$ is selected from phenyl, benzyl or pyridyl, optionally substituted with one or more of the electron-donating groups independently selected from the group consisting of —OH, methyl, ethyl, n-propyl, isopropyl, n-butyl, t-butyl, methoxy, ethoxy, n-propoxy, s-propoxy, n-butoxy, t-butoxy, methoxyethoxy, methoxymethyl, ethoxymethyl, propoxymethyl, dimethoxymethyl, butoxymethyl, methoxyethyl, ethoxyethyl, phenyl, benzyl, phenylethyl, phenylpropyl, phenylbutyl, acetoxyl, propionyloxyl, butyryloxyl, benzoyloxyl, —$NH_2$, methylamino, ethylamino, propylamino, isopropylamino, dimethylamino, diethylamino, dipropylamino, methylethylamino, 2-hydroxyethylamino, di(2-hydroxyethyl)amino, piperidino, morpholino, N-methylpiperadinyl, thiomorpholino, aziridinyl, indolinyl, tetrahydroquinolinyl and halogeno (including fluoro, chloro, bromo and iodo).

Preferably, $R^4$ is selected from phenyl, benzyl or pyridyl, optionally substituted with one or more of the electron-donating groups independently selected from the group consisting of para-methoxy, para-chloro, para-bromo, para-ethoxy, para-$NH_2$, para-phenyl, ortho-methoxy, ortho-chloro, ortho-bromo, ortho-ethoxy, ortho-$NH_2$ and ortho-phenyl.

Preferably, $R^4$ is mono-, di- or tri-substituted with an electron-donating group defined above, preferably mono-substituted.

Preferably, $R^4$ is selected from phenyl, para-methoxyphenyl, para-chlorophenyl, para-bromophenyl, para-ethoxyphenyl, para-aminophenyl and para-phenylphenyl.

$R^5$-$R^{12}$ are preferably independently selected from the group consisting of —H, —OH, —OC(O)$CH_3$, —OC(O)$CH_2CH_3$, $NH_2$, —NHC(O)$CH_3$, —NHC(O)$CH_2CH_3$, —$NHCH_3$, —$NHCH_2CH_3$ and a group

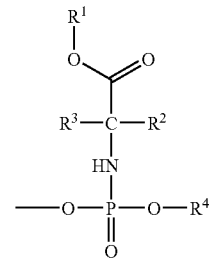

wherein $R^1$-$R^4$ are independently selected and are as defined above.

Preferably, at least one of groups $R^5$-$R^{12}$ is a —NHC(O)$CH_3$ group.

Preferably, $R^5$ is —OH, —OC(O)$CH_3$, —OC(O)$CH_2CH_3$, —NHC(O)$CH_3$ or —NHC(O)$CH_2CH_3$, $R^6$ is —OH, —$NH_2$, —NHC(O)$CH_3$ or —NHC(O)$CH_2CH_3$, $R^7$ is —OH or —OCH($CH_3$)C(O)OH, $R^8$ is —OH, $R^9$ is —H or —OH, $R^{10}$ is —OH, $R^{11}$ is —OH and $R^{12}$ is —OH.

$R^6$-$R^8$, $R^{11}$ and $R^{12}$ are preferably independently selected from the group consisting of —H, —OH, —$NHC_{1-10}$ alkyl, —NHC(O)$C_{1-10}$ alkyl and —$NH_2$.

$R^6$-$R^8$, $R^{11}$ and $R^{12}$ are preferably independently selected from the group consisting of —NHC(O)$C_{1-6}$ alkyl and —$NH_2$.

$R^6$ is preferably a —NHC(O)$CH_3$ group.

$R^6$-$R^8$, $R^{11}$ and $R^{12}$ are preferably —OH.

$R^5$ and $R^{10}$ are preferably independently selected from the group consisting of —OH and —$OC_{1-10}$ alkyl, wherein the alkyl chain may be substituted or unsubstituted, cyclic or acyclic.

$R^5$ and $R^{10}$ are preferably —OH.

Preferably, $R^5$ and $R^{10}$ do not comprise a halogen or a purine or pyrimidine base.

$R^{13}$, $R^{13'}$, $R^{14}$ and $R^{15}$ are preferably independently selected from the group consisting of —H, $C_{1-20}$ alkyl, $C_{2-20}$ alkenyl, $C_{2-20}$ alkynyl, $C_{3-30}$ cycloalkyl, $C_{3-30}$ cycloalkenyl, $C_{4-30}$ cycloalkynyl, $C_{7-30}$ aralkyl, $C_{7-30}$ alkaryl and $C_{5-30}$ aryl.

$R^{13}$, $R^{13'}$, $R^{14}$ and $R^{15}$ are more preferably independently selected from the group consisting of —H, $C_{1-15}$ alkyl, $C_{2-15}$ alkenyl, $C_{2-15}$ alkynyl, $C_{3-20}$ cycloalkyl, $C_{3-20}$ cycloalkenyl, $C_{4-20}$ cycloalkynyl, $C_{7-20}$ aralkyl, $C_{7-20}$ alkaryl and $C_{6-20}$ aryl.

$R^{13}$, $R^{13'}$, $R^{14}$ and $R^{15}$ are more preferably independently selected from the group consisting of straight chain $C_{1-10}$ alkyl, $C_{2-10}$ alkenyl and $C_{6-2}$ aryl.

Preferably, $R^{13}$, $R^{13'}$, $R^{14}$ and $R^{15}$ are independently selected from the group consisting of methyl, ethyl, propyl, butyl, hexyl, cyclohexyl, octyl, nonyl, dodecyl, eicosyl, norbornyl, adamantyl, vinyl, propenyl, cyclohexenyl benzyl, phenylethyl, phenylpropyl, phenyl, tolyl, dimethylphenyl, trimethylphenyl, ethylphenyl, propylphenyl, biphenyl, naphthyl, methylnaphthyl, anthryl, phenanthryl, benzylphenyl, pyrenyl, acenaphthyl, phenalenyl, aceanthrylenyl, tetrahydronaphthyl, indanyl, biphenyl and structural isomers thereof, preferably methyl, ethyl, propyl and isopropyl.

Preferred compounds (I) comprise monosaccharides (II) and (III) selected from the group consisting of galactosamine, fructose, glucosamine, n-acetylgalactosamine, galactose, n-acetylglucosamine, glucose, muramic acid, mannose, n-acetylmuramic acid and ribose, substituted with one or more groups (A):

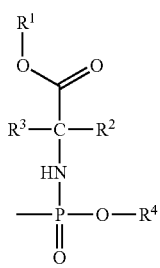

(A)

A preferred compound (I) is N-acetyl glucosamine substituted with a group (A).

wherein $R^1$-$R^4$ are independently selected and are as defined above.

Preferably, the present invention encompasses all possible optical isomeric forms of the groups (II) and (III). Preferably, the groups (II) and (III) are selected to resemble the predominant optical isomers in their naturally occurring monosaccharide analogues. Preferably, the chirality at each chiral centre of groups (II) and (I) is independently fixed in the R or S configuration. The chirality at each chiral centre of groups (II) and (III) may be of mixed configuration.

Preferably, the compounds of the present invention have an octanol/water partition coefficient (log P) in the range of 1-3, preferably 1.5-2.5, preferably about 2.

In a particularly preferred embodiment, X comprises a group having the structure (IV)

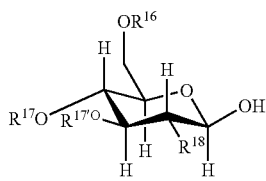

(IV)

wherein:
at least $R^{16}$ comprises a group (A)

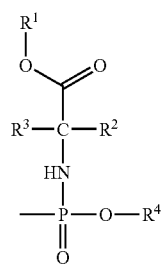

(A)

wherein $R^1$-$R^4$ are independently selected and are as defined above;

$R^{17}$ and $R^{17'}$ are independently selected from the group consisting of —H and a group (A);

$R^{18}$ is selected from the group consisting of —OH, —$OR^{19}$, halogen, —$SR^{19'}$, $N_3$, —$NR^{20}_2$ and —$NHR^{20}$, wherein $R^{19}$ and $R^{19'}$ are independently selected from the group consisting of —H, monovalent hydrocarbon radicals, protecting groups and —$C(O)R^{21}$, $R^{20}$ is selected from the group consisting of —H, monovalent hydrocarbon radicals, protecting groups and —$C(O)R^{21}$, wherein $R^{21}$ is selected from the group consisting of —H and monovalent hydrocarbon radicals;

or a pharmaceutically acceptable derivative or metabolite of a compound of formula (IV).

Preferably, when one of groups $R^{17}$ or $R^{17'}$ is a group (A), the other $R^{17}$ or $R^{17'}$ is —H.

$R^{17}$ and $R^{17'}$ are preferably —H.

$R^{18}$ is preferably selected from the group consisting of —OH, —$NH_2$ and —$NHC(O)R^{22}$, wherein $R^{22}$ is selected from the group consisting of $C_{1-20}$ alkyl, $C_{2-20}$ alkenyl, $C_{2-20}$ alkynyl, $C_{3-30}$ cycloalkyl, $C_{3-30}$ cycloalkenyl, $C_{4-30}$ cycloalkynyl, $C_{7-30}$ aralkyl, $C_{7-30}$ alkaryl and $C_{5-30}$ aryl.

$R^{18}$ is more preferably a group —$NHC(O)R^{22}$.

$R^{22}$ is preferably selected from the group consisting $C_{1-15}$ alkyl, $C_{2-15}$ alkenyl, $C_{2-15}$ alkynyl, $C_{3-20}$ cycloalkyl, $C_{3-20}$ cycloalkenyl, $C_{4-20}$ cycloalkynyl, $C_{7-20}$ aralkyl, $C_{7-20}$ alkaryl and $C_{6-20}$ aryl.

$R^{22}$ is more preferably selected from the group consisting of straight chain $C_{1-10}$ alkyl, straight chain $C_{2-10}$ alkenyl and $C_{6-8}$ aryl.

More preferably, $R^{22}$ is selected from the group consisting of methyl, ethyl, propyl, butyl, pentyl, hexyl, cyclohexyl, octyl, nonyl, dodecyl, eicosyl, norbornyl, adamantyl, vinyl, propenyl cyclohexenyl, benzyl, phenylethyl, phenylpropyl, phenyl, tolyl, dimethylphenyl, trimethylphenyl, ethylphenyl, propylphenyl, biphenyl, naphthyl, methylnaphthyl, anthryl, phenanthryl, benzylphenyl, pyrenyl, acenaphthyl phenalenyl, tetrahydronaphthyl, indanyl and biphenyl.

Preferably $R^{18}$ is —NHC(O)CH$_3$ or NHC(O)CH$_2$CH$_3$.

$R^{19}$, $R^{19'}$, $R^{20}$ and $R^{21}$ are preferably independently selected from the group consisting of —H, $C_{1-20}$ alkyl, $C_{2-20}$ alkenyl, $C_{2-20}$ alkynyl, $C_{3-30}$ cycloalkyl, $C_{3-30}$ cycloalkenyl, $C_{5-30}$ cycloalkynyl, $C_{7-30}$ aralkyl, $C_{7-30}$ alkaryl and $C_{5-30}$ aryl.

$R^{19}$, $R^{19'}$, $R^{20}$ and $R^{21}$ are more preferably independently selected from the group consisting of —H, $C_{1-15}$ alkyl $C_{2-15}$ alkenyl, $C_{2-15}$ alkynyl, $C_{3-20}$ cycloalkyl, $C_{3-20}$ cycloalkenyl, $C_{4-20}$ cycloalkynyl $C_{7-20}$ aralkyl, $C_{7-20}$ alkaryl and $C_{6-20}$ aryl.

$R^{19}$, $R^{19'}$, $R^{20}$ and $R^{21}$ are more preferably independently selected from the group consisting of straight chain $C_{1-10}$alkyl, straight chain $C_{2-10}$ alkenyl and $C_{6-18}$ aryl.

Preferably, $R^{19}$, $R^{19'}$, $R^{20}$ and $R^{21}$ are independently selected from the group consisting of methyl ethyl, propyl butyl, hexyl, cyclohexyl, octyl, nonyl, dodecyl, eicosyl norbornyl adamantyl, vinyl, propenyl, cyclohexenyl, benzyl, phenylethyl, phenylpropyl, phenyl tolyl, dimethylphenyl trimethylphenyl, ethylphenyl, propylphenyl, biphenyl, naphthyl, methylnaphthyl, anthryl phenanthryl, benzylphenyl, pyrenyl, acenaphthyl, phenalenyl aceanthrylenyl tetrahydronaphthyl indanyl, biphenylyl preferably methyl, ethyl, propyl and isopropyl.

Preferred electron donating groups which may comprise part of $R^4$ in compound (I) or (IV) as defined above, or compound (V) and (VI), as defined below, include $C_{1-20}$ alkyl, —NH$_2$, —NHR$^{23}$, —NR$^{24}_2$, —OH, —OR$^{25}$, —O$^-$, —NHC(O)R$^{26}$, —OC(O)R$^{27}$, —CH═CR$^{28}_2$, halogen (including F, Cl, Br and I), wherein $R^{23-28}$ are independently selected from the group consisting of $C_{1-20}$ alkyl, $C_{2-20}$ alkenyl, $C_{2-20}$ alkynyl, $C_{3-30}$ cycloalkyl, $C_{3-30}$ cycloalkenyl, $C_{4-30}$ cycloalkynyl, $C_{7-30}$ aralkyl, $C_{7-30}$ alkaryl and $C_{5-30}$ aryl.

More preferably, $R^{23-28}$ are independently selected from the group consisting of $C_{1-15}$ alkyl $C_{2-15}$ alkenyl, $C_{2-15}$ alkynyl, $C_{3-20}$ cycloalkyl, $C_{3-20}$ cycloalkenyl, $C_{4-20}$ cycloalkynyl, $C_{7-20}$ aralkyl, $C_{7-20}$ alkaryl and $C_{6-20}$ aryl.

More preferably, $R^{23-28}$ are independently selected from the group consisting of straight chain $C_{1-10}$ alkyl, straight chain $C_{2-10}$ alkenyl and $C_{6-12}$ aryl.

In a particularly preferred embodiment of the present invention, compound (I) has the structure (V)

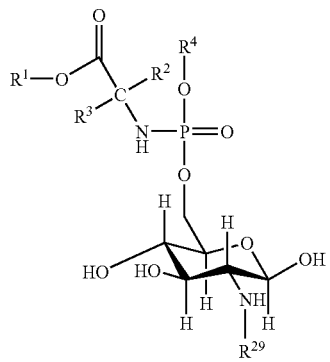

(V)

wherein:
$R^{29}$ is selected from the group consisting of —H, protecting groups and —C(O)R$^{30}$ wherein
$R^{30}$ is selected from the group consisting of —H, $C_{1-10}$ alkyl, $C_{2-10}$alkenyl and $C_{1-12}$ aryl;
$R^1$ is selected from the group consisting of —H, protecting groups, $C_{1-10}$ alkyl $C_{2-10}$ alkenyl, $C_{7-12}$ aralkyl, $C_{7-12}$ alkaryl and $C_{6-12}$ aryl;

$R^2$ and $R^3$ are independently selected from the group consisting of —H, methyl, propyl, isopropyl, butyl isobutyl, phenyl, hydroxyphenyl, indole, thiol, alkylthiol, thioalkyl, hydroxyalkyl, amine, amino, imino, alkylimino, alkyl-NH—, H$_2$N-alkyl-, imidazole, amide and carboxylate;

$R^4$ is selected from the group consisting $C_{7-18}$ aralkyl or $C_{6-12}$ aryl substituted with one or more electron donating groups;
or a pharmaceutically acceptable derivative or metabolite of a compound of formula (V).

Preferably, $R^{30}$ is —CH$_3$ or —CH$_2$CH$_3$, $R^2$ is preferably —H, $R^3$ is preferably —H, —CH$_3$, —CH$_2$CH$_3$ or —CH$_2$Ph (where Ph is phenyl).

According to a second aspect of the present invention, there is provided a process for the preparation of a compound of formula (I), the process comprising reacting a compound of formula (VI)

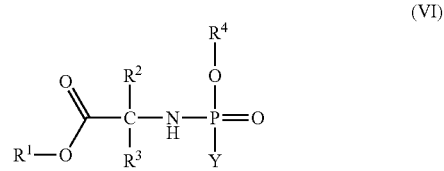

(VI)

wherein:
$R^1$-$R^4$ are independently selected and have the same definitions as above; and,
Y is a leaving group;
with a compound comprising the structure (VII) or (VIII)

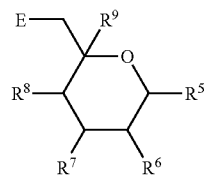

(VII)

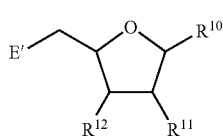

(VIII)

wherein:
E and E' are independently selected from nucleophilic groups capable of displacing a group Y from a compound of formula (VI); and
$R^5$-$R^{12}$ are independently selected and have the same definitions as above.

Preferably E and E' are both OH. In this embodiment, structures (VII) or (VIII) are represented by structures (IX) and (X) respectively as shown below.

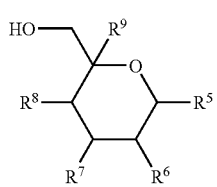

(IX)

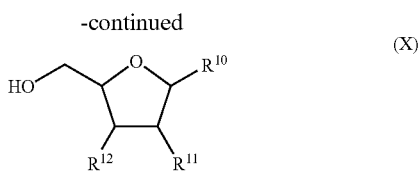

wherein:

$R^5$-$R^{12}$ are independently selected and have the same definitions as above.

The term "leaving group" generally refers to groups readily displaceable by a nucleophile. Such leaving groups are well known in the art. Examples of such leaving groups include, but are not limited to, N-hydroxysuccinimide, N-hydroxybenzotriazole, triflates, tosylates, mesylates, brosylates, and halides.

Y is preferably selected from Cl, Br and I, preferably Cl.

The process is preferably carried out in the presence of a solvent, preferably an organic solvent, preferably a dry organic solvent.

Preferred organic solvents include hydrocarbons, ethers, halogenated hydrocarbons, ketones, alcohols, nitrites, amines, esters, carbonates and mixtures thereof.

Preferred solvents include diethylether, tetrahydrofuran, diphenylether, anisole, dimethoxybenzene, pyridine, trimethylamine and triethylamine.

The process is preferably carried out below ambient temperature (25° C.). More preferably, the reaction is carried out below 0° C., more preferably below −20° C., preferably below −30° C.

The reaction is preferably carried out in the presence of a base, preferably an organic base. For example, N-methylimidazole is preferred.

The compounds of the present invention have been found to be particularly useful in the treatment of arthritis, particularly osteoarthritis.

As used herein, the term "monovalent hydrocarbon radicals" refers to any straight chain, branched, cyclic, acyclic, heterocylic, saturated or unsaturated radical, which contains a carbon backbone comprising one or more hydrogen atoms, optionally substituted with one or more heteroatoms in or on the carbon backbone. The term "monovalent hydrocarbon radical" is intended to encompass the terms "alkyl", "alkenyl", "alkynyl", "cycloalkyl", "cycloalkenyl", "cycloalkynyl", "alkaryl", "aralkyl" and "aryl" as defined below.

As used herein, the term "alkyl" refers to a straight or branched saturated monovalent hydrocarbon radical, having the number of carbon atoms as indicated, optionally substituted with one or more heteroatoms in or on the carbon backbone.

As used herein, the term "alkenyl" refers to a straight or branched unsaturated monovalent hydrocarbon radical, having the number of carbon atoms as indicated, optionally substituted with one or more heteroatoms in or on the carbon backbone, and the distinguishing feature of a carbon-carbon double bond.

As used herein, the term "alkynyl" refers to a straight or branched unsaturated monovalent hydrocarbon radical, having the number of carbon atoms as indicated, optionally substituted with one or more heteroatoms in or on the carbon backbone, and the distinguishing feature of a carbon-carbon triple bond.

As used herein, the term "cycloalkyl" refers to a cyclic saturated monovalent hydrocarbon radical, having the number of carbon atoms as indicated, optionally substituted with one or more heteroatoms in or on the carbon backbone.

As used herein, the terms "cycloalkenyl" and "cycloalkynyl" refer to cyclic unsaturated monovalent hydrocarbon radicals, optionally substituted with one or more heteroatoms in or on the carbon backbone. A "cycloalkenyl" is characterized by a carbon-carbon double bond and a "cycloalkynyl" is characterized by a carbon-carbon triple bond.

As used herein, the term "aryl" refers to a monovalent unsaturated aromatic carbocyclic radical having one or two rings, optionally substituted with one or more heteroatoms in or on the carbon backbone, such as phenyl, naphthyl, indanyl or biphenyl, or to a monovalent unsaturated aromatic heterocyclic radical, optionally substituted with one or more heteroatoms in or on the carbon backbone, such as quinolyl, dihydroisooxazolyl, furanyl, imidazolyl, pyridyl, phthalimido, thienyl, thiophenyl, pyrrolyl and the like. Exemplary heterocyclic radicals include pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, napthridinyl, cinnolinyl, quinazolinyl, pyridopyridyl, benzoxazinyl, quinoxadinyl, chromenyl, chromanyl, isochromanyl and carbolinyl. Where the aryl group comprises more than one ring, the rings may be flied or bicyclic.

As used herein, the term "alkaryl" refers to an aryl group with an alkyl substituent, such as toluoyl. Binding is through the aryl group. Such groups have the number of carbon atoms as indicated, and may be substituted with one or more heteroatoms in or on the carbon backbone.

As used herein, the term "aralkyl" refers to an alkyl group with an aryl substituent, such as benzyl. Binding is through the alkyl group. Such groups have the number of carbon atoms as indicated, and may be substituted with one or more heteroatoms in or on the carbon backbone.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

As used herein, the term "heteroatom" includes N, O, S, P, Si and halogen (including F, Cl, Br and I).

As used herein, the term "protecting group" refers to any group which when bound to one or more hydroxyl groups, amine groups or carboxyl groups prevents reactions from occurring at these groups and which protecting group can be removed by conventional chemical or enzymatic steps to re-establish the hydroxyl, carboxyl or amine group.

As used herein, the term "amine-protecting group" as used herein refers to substituents of the amine group commonly employed to block or protect an amine group while reacting other functional groups in the molecule.

Examples of such amine-protecting groups include the formyl ("For") group, the trityl group, the phthalimido group, the trichloroacetyl group, the chloroacetyl, bromoacetyl, and iodoacetyl groups, urethane-type blocking groups, such as t-butoxycarbonyl ("Boc"), 2-4 biphenylyl)propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluoyl)propyl-2-oxycarbonyl, cyclopentanyloxycarbonyl, 1-methylcyclopentanyloxycarbonyl cyclohexanyloxycarbonyl, 1-methylcyclohexanyloxycarbonyl, 2-methylcyclohexanyloxycarbonyl, 2-(4-toluoylsulfonyl)ethoxycarbonyl, 2-(methylsulfonyl)ethoxycarbonyl, 2-triphenylphosphino)ethoxycarbonyl, 9-fluorenylmethoxycarbonyl ("Fmoc"), 2-(trimethylsilyl)ethoxycarbonyl, allyloxycarbonyl, 1-trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, .alpha.-2,4,5-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl and the like; the benzoylmethylsulfonyl group, dithiasuccinoyl ("Dts"), the 2-(nitro) phenylsulfenyl group ("Nps"), the diphenyl-phosphine oxide group and like amine-protecting groups. Preferred amine-protecting groups are Boc, Cbz and Fmoc.

As used herein, the term "hydroxy-protecting group" refers to a group commonly employed to block or protect a hydroxyl group while reacting other functional groups in the molecule.

Examples of hydroxy-protecting groups include tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl trimethylsilyl, (t-butyl)dimethylsilyl, 2,2,2-trichloroethoxycarbonyl groups and the like.

As used herein, the term "carboxyl-protecting group" as used herein refers to one of the ester derivatives of the carboxylic acid group commonly employed to block or protect the carboxylic acid group while reactions are carried out on other functional groups in the compound. Examples of such carboxylic acid protecting groups include t-butyl, benzyl, 4 nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties.

By "a pharmaceutically acceptable derivative" is meant any pharmaceutically acceptable salt, ester or salt of such ester or any other compound which, upon administration to a recipient, is capable of providing (directly or indirectly) a compound (I), (IV) or (V).

Pharmaceutically acceptable salts are generally acid addition salts, which are preferably such of therapeutically acceptable inorganic or organic acids, such as strong mineral acids, for example hydrohalic. Preferred salts include hydrochloric acid, hydrobromic acid, sulfuric acid, phosphoric acid, nitric acid, aliphatic or aromatic carboxylic or sulfonic acids, for example, formic acid, acetic acid, propionic acid, succinic acid, glycollic acid, lactic acid, malic acid, tartaric acid, gluconic acid, citric acid, maleic acid, fumaric acid, pyruvic acid, phenylacetic acid, benzoic acid, 4-aminobenzoic acid, anthranilic acid, 4-hydroxybenzoic acid, salicylic acid, 4-aminosalicylic acid, pamoic acid, nicotinic acid, methanesulfonic acid, ethanesulfonic acid, hydroxyethanesulfonic acid, benzenesulfonic acid, p-toluenesulfonic acid, naphthalenesulfonic acid, sulfanilic acid, cyclohexylsulfamic acid and ascorbic acid. For compounds having a free carboxy group, pharmaceutically acceptable salts are also derived from bases, for example, alkali metal salts, such as the sodium salt, or salts derived from pharmaceutically acceptable amines.

The terms "derivative" and "metabolite", as used herein with reference to compounds (I), (IV) and (V), do not include naturally occurring saccharide metabolites, for example, glucose-6-phosphate, fructose-phosphate and glucosamine-6-phosphate.

According to a further aspect of the present invention there is provided a pharmaceutical composition comprising a compound of the present invention in combination with a pharmaceutically acceptable excipient.

According to a further aspect of the present invention there is provided a method of preparing a pharmaceutical composition comprising the step of combining a compound of the present invention with a pharmaceutically acceptable excipient.

The compounds of the present invention may be used in a method of medical treatment, of the human or animal body, by way of therapy.

The compounds of the present invention may be used in a method of preparing a medicament, used in the treatment of arthritis, preferably osteoarthritis.

The compounds of the present invention may be used in a method of preparing a medicament, used in the treatment of cancer.

The compounds of the present invention may be used in a method of preparing a medicament, used in the treatment of pain.

The compounds of the present invention may be used in a method of preparing a medicament, used in the treatment of muscaloskeletal conditions.

The compounds of the present invention may be used in a method of preparing a medicament, used in the treatment of diabetes.

The compounds of the present invention may be used in a method of preparing a medicament, used in the treatment of neurodegenerative disease.

The compounds of the present invention may be used in a method of preparing a medicament, used in the treatment of Alzheimers disease.

The present invention further provides a method of treating a patient for arthritis, preferably osteoarthritis, comprising administering a therapeutically effective amount of a compound according to the present invention.

The present invention further provides a method of treating a patient for cancer, comprising administering a therapeutically effective amount of a compound according to the present invention.

The present invention further provides a method of treating a patient for pain, comprising administering a therapeutically effective amount of a compound according to the present invention.

The present invention further provides a method of treating a patient for a muscaloskeletal condition, comprising administering a therapeutically effective amount of a compound according to the present invention.

The present invention further provides a method of treating a patient for diabetes, comprising administering a therapeutically effective amount of a compound according to the present invention.

The present invention further provides a method of treating a patient for a neurodegenerative disease, comprising administering a therapeutically effective amount of a compound according to the present invention.

The present invention further provides a method of treating a patient for Alzheimers disease, comprising administering a therapeutically effective amount of a compound according to the present invention.

The medicament employed in the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Formulations for rectal administration may be presented as a suppository with a suitable base comprising for example cocoa butter or a salicylate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.01 to 10 mg per kilogram body weight of the recipient per day, preferably in the range of 0.2 to 1.0 mg per kilogram body weight per day. The desired dose is preferably presented once daily, but may be dosed as two, three, four, five or six or more sub-doses administered at appropriate intervals throughout the day. These sub-doses may be administer in unit dosage forms, for example, containing 10 to 1500 mg, preferably 20 to 1000 mg, and preferably 50 to 700 mg of active ingredient per unit dosage form.

The invention will now be described with reference to the following Examples. It will be appreciated that what follows is by way of example only and that modifications to detail may be made whilst still falling within the scope of the invention.

EXPERIMENTAL

General Methods

Thin Layer Cromatography: Thin layer cromatography (TLC) was performed on commercially available Merck Kieselgel plates and separated components were visualised using ultra violet light (245 and 366 nm).

Column Chromatography Column chromatography was performed using Woelm silica (32-63 mm) as stationary phase. Glass columns were slurry packed in the appropriate eluent under gravity. Samples were applied as a concentrated solution in the same eluent, or pre-absorbed onto silica gel. Fractions containing the product were identified by TLC, pooled and the solvent removed in vacuo.

NMR Spectroscopy: $^1$H, $^{13}$C, $^{31}$P and $^{19}$F were recorded on a Bruker Avance DPX300 spectrometer with operating frequencies of 300, 75, 121 and 282 MHz respectively. $^{31}$P-NMR are reported in units of δ relative to 85% phosphoric acid as the external standard, positive shifts are downfield. The following abbreviations are used in the assignment of NMR signals: s (singlet), d (doublet), t (triplet), q (quartet), bs (broad signal) dd (doublet of doublets).

Solvents and Reagents: All solvents used were anhydrous and used as purchased from Aldrich. All reagents were used as received. All glassware was oven dried at 130° C. for several hours or overnight and allowed to cool under a steam of dry nitrogen.

Preparation of
Phenyl(Methoxy-L-alaninyl)phosphorochloridate

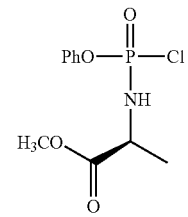

Phenyl dichlorophosphate (3.54 ml, 23.7 mmol) and L-alanine-methyl ester hydrochloride salt (3.29 g, 23.7 mmol) were suspended in anhydrous 30 ml of DCM. Anhydrous triethylamine (6.5 ml, 47.4 mmol) in 20 ml of dry DCM was added dropwise at −78° C. under nitrogen. Following the addition, the reaction mixture was slowly allowed to warm at room temperature and stirred for one hour. The solvent was removed under reduced pressure and the solid obtained was washed with anhydrous ether (2×20 ml), filtered and the filtrate reduced to dryness to give the crude product (6.05 g, 92%) as an oil, which was used in the following step without any further purification.

$^{31}$P nmr (CDCl$_3$, 121 MHz): 9.16, 8.82.

Preparation of N-Acetylglucosamine-6-[phenyl (methoxy-L-alanyl)]phosphoramidate [GLU3]

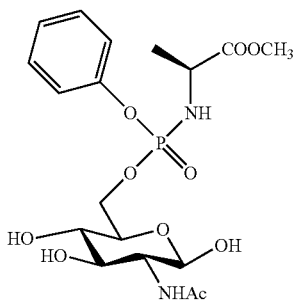

To a suspension of N-acetylglucosamine (1.5 g, 6.78 mmol) in 100 ml of anhydrous pyridine under an atmosphere of argon at 40° C. N-methylimidazole (2.7 ml, 33.9 mmol) was added.

Phenyl(methoxy-L-alaninyl)phosphorochloridate (2.25 g, 8.13 mmol) in 12 ml of dry THF was then added dropwise over 15 minutes, and the reaction mixture was stirred at room temperature at 40° C. for 2 hours. The solvent was removed under reduced pressure and the residue was purified by column cromatography using an eluent of DCM/MeOH (98:2), followed by an eluent of DCM/MeOH (9:1), to give the pure product (100 mg, 3%) as a white foam.

$^1$H-nmr (d$_6$-DMSO; 300 MHz): 7.70 (1H, d, J=8.0 Hz, NH), 7.41-7.16 (5H, m, OPh), 6.61 (1H, m, OH-1), 5.93 (1H, m, NH-Ala), 5.20 (1H, m, OH-4), 4.97 (1H, m, H-1), 4.77 (1H, d, J=4.77, 3-OH), 4.24 and 4.07 (2H, m, H-6), 3.85 (2H, m, CH-Ala+H-5), 3.66-3.44 (5H, m, COOCH$_3$+H-2+H-3), 3.15 (1H, m, H-4), 1.85 (3H, s, NHCOCH$_3$), 1.23 (3H, m, CH$_3$-Ala).

13C-nmr (d$_6$-DMSO; 75 MHz): 20.0 (CH$_3$-Ala), 23.0 (23.1 NHCOCH$_3$), 49.9 and 50.0 (CH-Ala), 52.1 and 52.2 (COOCH$_3$), 54.5 (C-2), 66.3 (C-6), 70.4, 70.5, 70.6, 70.7 (C-5 and C-3), 71.1 (C-4), 91.1 (C-1), 120.4 and 120.5, 124.7, 129.7 and 129.9, 151.0 and 151.1 (OPh), 169.7 and 169.9 (NHCOCH$_3$), 173.9 and 170.0 (COOCH$_3$).

$^{31}$P nmr (CDCl$_3$, 121 MHz): 4.88, 4.54.

Preparation of N-Acetylglucosamine-3,6-[phenyl (methoxy-L-alanyl)]bis-phosphoramidate [GLU2]

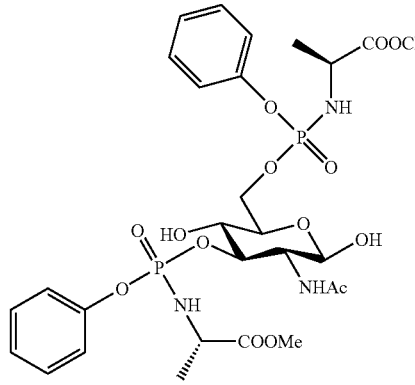

This was also isolated from the above reaction as a white foam (400 mg, 8%).

$^1$H-nmr (d$_6$-DMSO; 300 MHz): 7.71 (1H, d, J=8.1H, NH), 7.36 and 7.17 (10H, m, 2×OPh), 6.99 (1H, m, OH-1), 5.99 (2H, m, NH-Ala), 5.53 (1H, m, OH-4), 5.01 (1H, m, H-1), 4.43-4.13 (3H, m, H-3+H-6), 3.90 (4H, m, 2×CH-Ala, +H-5+H-2), 3.57 (7H, m, 2×COOCH$_3$+H-4), 7.76 (3H, s, NHCOCH$_3$), 1.24 (6H, m, 2×CH$_3$-Ala).

$^{13}$C-nmr (d$_6$-DMSO; 75 MHz): 20.0 (CH$_3$-Ala), 22.9 (NHCOCH$_3$), 50.0 and 50.1 (CH-Ala), 52.1 (COOCH$_3$), 53.0 (C-2), 65.7 (C-6), 69.5, 70.3, 78.3 (C-5, C-4, C-3), 91.2 (C-1), 120.5, 120.5, 124.8, 129.8, 129.9, 151.1, 151.1, 159.3 (2×OPh), 169.8 (NHCOCH$_3$), 174.1 (COOCH$_3$).

$^{31}$P nmr (CDCl$_3$, 121 MHz): 632, 6.22, 5.57, 4.64.

Preparation of 4-Methoxyphenyl phosphorodichloridate

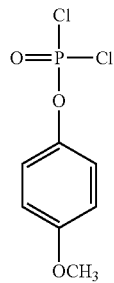

Dry triethylamine (4.2 ml, 30 mmol) and p-methoxyphenol (3.72 g, 30 mmol) in 100 ml dry ether were added dropwise to a stirred solution of dry ether (50 ml) containing phosphorus oxychloride (2.80 ml, 30 mmol), at −78° C. under nitrogen. Following the addition, the reaction mixture was slowly allowed to warm at room temperature and stirred for one hour. The solvent was removed under reduced pressure to give the crude product (6.6 g, 92%) as an oil, which was used in the following step without any further purification.

$^{31}$P nmr (CDCl$_3$, 121 MHz): 5.4

Preparation of 4-methoxyphenyl(benzoxy-L-alaninyl) phosphorochloridate

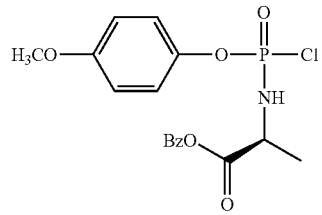

4-Methoxyphenyl phosphorodichloridate (6.6 g, 27.38 mmol) and L-alanine-benzyl ester hydrochloride salt (5.91 g, 27.38 mmol) were suspended in 100 ml of anhydrous DCM. Anhydrous triethylamine (7.6 ml, 57.77 mmol) in 20 ml of dry DCM was added dropwise at −78° C. under nitrogen. Following the addition, the reaction mixture was slowly allowed to warm at room temperature and stirred for one hour. The solvent was removed under reduced pressure and the solid obtained was washed with anhydrous ether (2×20 ml), filtered and the filtrate reduced to dryness to give the crude product (9.66 g, 92%) as an oil, which was used in the following step without any further purification.

31P nmr (CDCl$_3$, 121 MHz): 9.8, 9.5

Preparation of N-Acetylglucosamine-6-[4-methoxyphenyl(benzoxy-L-alanyl)]phosphoramidate [GLU5]

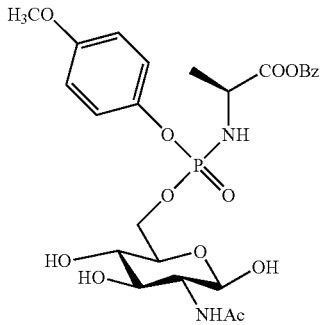

To a suspension of N-acetylglucosamine (2.0 g, 9.04 mmol) in 100 ml of anhydrous pyridine under an atmosphere of argon at −40° C. N-methylimidazole (3.6 ml, 45.25 mmol) was added. 4-methoxyphenyl(benzoxy-L-alaninyl)phosphorochloridate (4.16 g, 10.8 mmol) in 8.6 ml of dry THF was then added dropwise over 15 minutes, and the reaction mixture was stirred at room temperature at 40° C. for 2 hours. The solvent was removed under reduced pressure and the residue was purified by column cromatography using an eluent of DCM/MeOH (98:2), followed by an eluent of DCM/MeOH (9:1), to give the pure product (400 mg, 9%) as a white foam.

$^1$H-nmr (d6-DMSO; 300 MHz): 7.74 (1H, d, J=7.8 Hz, NH), 7.43 and 7.42 (5H, $s_{app}$, Bz), 7.18-6.91 (4H, m, OPh), 6.65 (1H, m, OH-1), 5.94 (1H, m, NH-Ala), 5.27-5.11 (3H, m, OH-4+CH$_2$Bz), 5.01 (1H, m, H-1), 4.81 (1H, m, 3-OH), 4.26 and 4.09 (2H, m, H-6), 3.94 (2H, m, CH-Ala+H-5), 3.77 (1H, s, OCH$_3$), 3.69 (1H, m, H-2), 3.61 (1H, m, H-3) 3.17 (1H, m, H-4), 1.90 (3H, s, NHCOCH$_3$) 1.23 (3H, m, CH$_3$-Ala).

$^{13}$C-nmr (d$_6$-DMSO; 75 MHz): 20.0 and 20.1 (CH$_3$-Ala), 23.0 (23.1 NHCOCH$_3$) 50.1 and 50.2 (CH-Ala), 545 (C-2), 66.3 and 66.3 (CH$_2$Bz+C-6), 70.5, 70.7, 71.1 (C-4+C-5+C-3), 91.1 (C-1), 114.8, 121.5 and 121.5, 128.2, and 128.2, 128.4, 128.8, 136.3, 144.6, 156.2 (OPh+Bz), 169.7 (NH COCH$_3$), 173.40 (COOBz).

31P nmr (CDCl$_3$, 121 MHz): 5.53, 5.41.

Biological Assay:

Method: Articular cartilage was harvested under aseptic conditions from the metatarso-phalangeal joints (hock joints) of skeletally mature cattle (18 months or older). The articular cartilage was diced into small pieces and pre-cultured for 2-3 days in 10% foetal calf serum, Dulbeco's Modified Eagle's Medium (DMEM) containing 50 µg/ml gentamycin. After pre-culture, the cartilage slices were washed 3 times in DMEM and then apportioned into 24 well culture plates at 10-20 mg cartilage per well in 0.5 ml media containing either DMEM alone (control) or DMEM plus glucosamine or chemically modified glucosamine derivatives of the present invention (Treated) at 2.5, 5, 10 and 15 mM concentrations and they were pre-cultured for a further 30-60 minutes in the presence or absence of these derivatives. A replicate set of these cultures was then exposed to 10 ng/ml interleukin-1 (IL-1α) and cultured for a further 4-6 days. Each experimental culture condition was set up in triplicate. Thus, the experimental culture conditions tested were:
(i) Control: DMEM alone;
(ii) Treated: DMEM+glucosamine or modified glucosamine at 2.5, 5, 10 and 15 mM concentrations;
(iii) Control+IL-1α: DMEM+10 ng/ml IL-1α; and,
(iv) Treated+IL-1α: DMEM+glucosamine or modified glucosamine at 2.5, 5, and 15 mM concentrations+10 ng/ml IL-1α.

At the end of 4-6 days culture, the media was separated from the pieces of tissue explant and one or more of the following analyses was performed:
(i) Analyses of media for sulphated glucosaminoglycan release (a measure of cartilage proteoglycan degradation) were performed using the dimethylmethylene blue (DMMB) method described by Farndale et al, (1986) Biochem. Biophys. Acta 883: 173-177;
(ii) Lactate levels in the media (a measure for cell viability and metabolism) were performed according to the method described by Curtis et al, (2002), Proceedings of the Nutrition Society 61:3871-389;
(iii) Western Blot analyses of media samples using mAbs BC-3 and BC-14 to detect cartilage proteoglycan (aggrecan) metabolites degraded by either aggrecanases (ADAMTS-4 & -5) or matrix metalloproteinases, respectively, can be performed according to the method described by Caterson et al, (2000) Matrix Biology 19:333-344;
(iv) Cartilage explants can be extracted with TriReagent (Sigma) to isolate RNA and DNA and following purification on Quiagen columns, are analysed by RT-PCR for gene profile expression of various cartilage matrix proteins: e.g. proteoglycans, collagens, aggrecanases (ADAMTS-4 & -5) and matrix metalloproteinases; Curtis et al, (2002) Arthritis and Rheumatism 46:1544-1553;
(v) Cartilage explants can be also extracted with 4 M guanidine HCl and the matrix proteins and proteoglycans are analysed by Western Blot analyses; Little et al, (2002) Matrix Biology 21: 271-288; and
(vi) A replicate set of cultures was used for radio-labelled sulphate incorporation to measure cartilage proteoglycan biosynthesis and cartilage metabolism.

The invention claimed is:

1. A phosphoramidate compound, comprising the structure (IV)

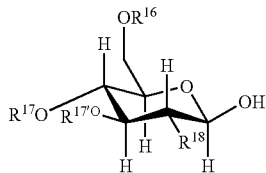

wherein:
R$^{16}$ is a group having the structure (A)

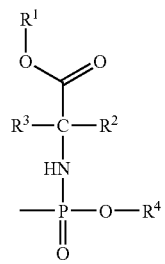

wherein:
R$^1$-R$^4$ are independently selected and
R$^1$ is selected from the group consisting of —H, C$_{1-20}$ alkyl, C$_{2-20}$ alkenyl, C$_{2-20}$ alkynyl, C$_{3-30}$ cycloalkyl, C$_{3-30}$ cycloalkenyl, C$_{7-30}$ aralkyl, C$_{7-30}$ alkaryl and C$_{5-30}$ aryl;
R$^2$ and R$^3$ are independently selected from the group consisting of —H, C$_{1-20}$ alkyl, C$_{2-20}$ alkenyl, C$_{2-20}$ alkynyl, C$_{3-30}$ cycloalkyl, C$_{3-30}$ cycloalkenyl, C$_{7-30}$ aralkyl, C$_{7-30}$ alkaryl, and C$_{5-30}$ aryl, or R$^2$ and R$^3$ together form an alkylene or heteroalkylene chain so as to provide, together with the C atom to which they are attached, a $C_{3-8}$ cycloalkyl, or $C_{3-8}$ cycloalkenyl group;

$R^4$ is selected from the group consisting of —H, $C_{1-20}$ alkyl, $C_{2-20}$ alkenyl, $C_{2-20}$ alkynyl, $C_{3-30}$ cycloalkyl, $C_{3-30}$ cycloalkenyl, $C_{7-30}$ aralkyl $C_{7-30}$ aralkyl, $C_{5-30}$ aryl, wherein $R^4$ is optionally mono-, di- or tri-substituted with groups independently selected from the group consisting of —OH, menthyl, ethyl, n-propyl, isopropyl, n-butyl, methoxy, ethoxy, n-propoxy, s-propoxy, n-butoxy, t-butoxy, methoxyethoxy, methoxymethyl, ethoxymethyl, propoxymethyl, dimethoxymethyl, butoxymethyl, methoxyethyl, ethoxyethyl, phenyl, benzyl, phenylethyl, phenylopropyl, phenylbutyl, acetoxyl, propionyloxyl, butyryloxyl, benzoyloxyl, —NH$_2$, methylamino, ethylamino, propylamino, isopropylamino, dimethylamino, diethylamino, dipropylamino, methylethylamino, 2-hydroxyethylamino, di(2-hydroxyethyl)amino, piperidino, morpholino, N-methylpiperadinyl, thiomorpholino, aziridinyl, indolinyl, tetrahydroquinolinyl and halogeno;

$R^{17}$ and $R^{17'}$ are independently selected from the group consisting of —H and the group (A); and $R^{18}$ is —NHC(O)CH$_3$;

or a pharmaceutically acceptable salt thereof.

2. The compound according to claim 1, or a pharmaceutically acceptable salt thereof, wherein $R^2$ is —H and $R^3$ is methyl.

3. The compound according to claim 1, or pharmaceutically acceptable salt thereof, wherein $R^1$ is selected from the group consisting of $C_{1-16}$ alkyl, $C_{2-16}$ alkenyl, $C_{2-16}$ alkynyl, $C_{3-20}$ cycloalkyl, $C_{3-20}$ cycloalkenyl, $C_{7-20}$ aralkyl, $C_{7-20}$ aralkyl and $C_{6-20}$ aryl.

4. The compound according to claim 1, or pharmaceutically acceptable salt thereof, wherein $R^1$ is selected from the group consisting of primary or secondary $C_{1-6}$ alkyl, $C_{2-6}$ alkenyl, $C_{5-7}$ cycloalkyl, $C_{5-7}$ cycloalkenyl, $C_{5-11}$ ar-$C_{1-6}$ alkyl, $C_{1-6}$ alk-$C_{5-11}$ aryl and $C_{5-11}$ aryl.

5. A compound according to claim 1, or a pharmaceutically acceptable salt thereof, wherein $R^1$ is selected from the group consisting of methyl, ethyl, propyl, butyl, hexyl, cyclohexyl, octyl, nonyl, dodecyl, eicosyl, norbornyl, adamantyl, vinyl, propenyl, cyclohexenyl, benzyl, phenylethyl, phenylpropyl, phenyl, tolyl, dimethylphenyl, trimethylphenyl, ethylphenyl, propylphenyl, biphenyl, naphthyl, methylnaphthyl, anthryl, phenanthryl, benzylphenyl, pyrenyl, acenaphthyl, phenalenyl, aceanthrylenyl, tetrahydronaphthyl, indanyl, and biphenyl.

6. A compound according to claim 1, or a pharmaceutically acceptable salt thereof, wherein $R^1$ is selected from the group consisting of methyl, ethyl, 2-butyl, benzyl.

7. The compound according to claim 1, or a pharmaceutically acceptable salt thereof, wherein $R^2$ and $R^3$ are independently selected from the group consisting of —H, primary, secondary and tertiary $C_{1-6}$ alkyl, $C_{5-7}$ ar-$C_{1-3}$ alkyl and $C_{1-3}$ alk-$C_{5-7}$ aryl.

8. A compound according to claim 1, or a pharmaceutically acceptable salt thereof, wherein at least one of $R^2$ and $R^3$ is selected from the group consisting of —H, methyl, propyl, isopropyl, butyl, isobutyl, phenyl, hydroxyphenyl, indolyl, thiol, alkylthio, thioalkyl, hydroxyalkyl, amino, alkylimino, imino, alkyl-NH—, H$_2$N-alkyl-, imidazolyl, amido and carboxyl.

9. The compound according to claim 1, or pharmaceutically acceptable salt thereof, wherein $R^2$ and $R^3$ are independently selected from the group consisting of —H, methyl, benzyl, isopropyl, propyl, n-butyl, s-butyl, t-butyl, or, $R^2$ and $R^3$ together form an alkylene or heteroalkylene chain so as to provide, together with the C atom to which they are attached, a group selected from $C_{3-6}$ cycloalkyl, $C_{3-6}$ cycloalkenyl.

10. The compound according to claim 1, or pharmaceutically acceptable salt thereof, wherein $R^2$ is —H or methyl.

11. The compound according to claim 1, or pharmaceutically acceptable salt thereof, wherein both $R^2$ and $R^3$ are methyl.

12. The compound according to claim 1, or pharmaceutically acceptable salt thereof, wherein both $R^2$ and $R^3$ together form a cyclopentyl ring.

13. The compound according to claim 1, or pharmaceutically acceptable salt thereof, wherein one or both of $R^2$ and $R^3$, either taken separately or together, corresponds to the side chains of any naturally occurring amino acid.

14. The compound according to claim 1, or pharmaceutically acceptable salt thereof, wherein the group —NH—CR$^2$R$^3$—CO$_2$R$^1$ is a —NH—CHR$^3$—CO$_2$R$^1$ group, which corresponds to a carboxy-protected α-amino acid.

15. The compound according to claim 1, or pharmaceutically acceptable salt thereof, wherein $R^4$ is selected from the group consisting of $C_{1-15}$ alkyl, $C_{2-15}$ alkenyl, $C_{2-15}$ alkynyl, $C_{3-20}$ cycloalkyl, $C_{3-20}$ cycloalkenyl, $C_{7-20}$ aralkyl, $C_{7-20}$ alkaryl and $C_{6-20}$ aryl.

16. The compound according to claim 1, or pharmaceutically acceptable salt thereof, wherein $R^4$ is selected from the group consisting of substituted or unsubstituted $C_{7-12}$ alkaryl, substituted or unsubstituted $C_{7-12}$ aralkyl and substituted or unsubstituted $C_{6-12}$ aryl.

17. The compound according to claim 1 or pharmaceutically acceptable salt thereof, wherein $R^4$ is selected from the group consisting of phenyl, benzyl and pyridyl, optionally substituted with one or more groups independently selected from the group consisting of —OH, methyl, ethyl, n-propyl, isopropyl, n-butyl, t-butyl, methoxy, ethoxy, n-propoxy, s-propoxy, n-butoxy, t-butoxy, methoxyethoxy, methoxymethyl, ethoxymethyl, propoxymethyl, dimethoxymethyl, butoxymethyl, methoxyethyl, ethoxyethyl, phenyl, benzyl, phenylethyl, phenylpropyl, phenylbutyl, acetoxyl, propionyloxyl, butyryloxyl, benzoyloxyl, —NH$_2$, methylamino, ethylamino, propylamino, isopropylamino, dimethylamino, diethylamino, dipropylamino, methylethylamino, 2-hydroxyethylamino, di(2-hydroxyethyl)amino, piperidino, morpholino, N-methylpiperidinyl, thiomorpholino, aziridinyl, indolinyl, tetrahydroquinolinyl and halogeno.

18. The compound according to claim 1, or a pharmaceutically acceptable salt thereof, wherein $R^4$ is selected from phenyl, benzyl or pyridyl, optionally substituted with one or more groups independently selected from the group consisting of para-methoxy, para-chloro, para-bromo, para-ethoxy, para-NH$_2$, para-phenyl, ortho-methoxy, ortho-chloro, ortho-bromo, ortho-ethoxy, ortho-NH$_2$ and ortho-phenyl.

19. A process for the preparation of a compound of formula (I), or a pharmaceutically acceptable salt thereof, the process comprising reacting a compound of formula (VI)

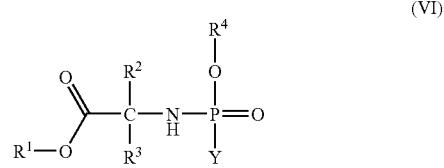

(VI)

wherein:

$R^1$-$R^4$ are independently selected and are as defined in claim 1; and,

Y is selected from the group consisting of triflate, tosylate, mesylate, brosylate, and halide;

with a compound comprising the structure
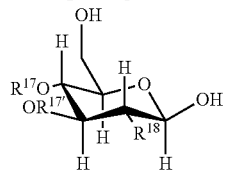
wherein:
$R^{18}$, $R^{17}$ and $R^{17'}$ are independently selected and are defined in claim 1.
20. The process according to claim 19, wherein Y is selected from chloro, bromo, and iodo.
* * * * *

UNITED STATES PATENT AND TRADEMARK OFFICE
CERTIFICATE OF CORRECTION

PATENT NO. : 8,119,779 B2
APPLICATION NO. : 10/586101
DATED : February 21, 2012
INVENTOR(S) : Christopher McGuigan et al.

It is certified that error appears in the above-identified patent and that said Letters Patent is hereby corrected as shown below:

Title Page, Item [56], Col. 2, Other Publications, delete "Chrondroprotective" and insert --Chondroprotective--, therefor.

Title Page, Item [56], Col. 2, Other Publications, delete "Antisteoarthritis" and insert --Antiosteoarthritis--, therefor.

In Col. 6, chemical structure (IV), lines 3-13 should read,

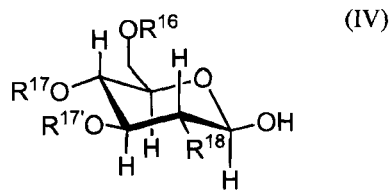

In Claim 1, Col. 18, lines 3-13, chemical structure (IV), should read,

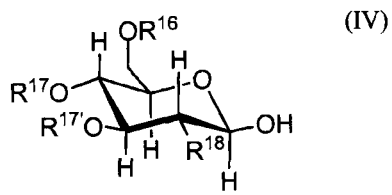

In Claim 1, Col. 18, Line 34 and Claim 19, Col. 21, Line 1, delete each occurrence of "comprising" and insert --having--, therefor.

In Claim 1, Col. 19, Line 6, delete "$C_{7-30}$ aralkyl $C_{7-30}$ aralkyl, $C_{5-30}$" and insert --$C_{7-30}$ aralkyl, $C_{7-30}$ alkaryl, and $C_{5-30}$--, therefor.

Signed and Sealed this
Twenty-eighth Day of August, 2012

David J. Kappos
*Director of the United States Patent and Trademark Office*

In Claim 1, Col. 19, Line 9, delete "menthyl," and insert --methyl,--, therefor.

In Claim 1, Col. 19, Line 10, after "n-butyl," insert --t-butyl,--.

In Claim 1, Col. 19, Line 14, delete "phenylopropyl," and insert --phenylpropyl,--, therefor.

In Claim 1, Col. 19, Line 15, delete "benzoyloxyl,—NH$_2$," and insert --benzoyloxyl, —NH$_2$,--, therefor.

In Claim 1, Col. 19, Lines 19-20 (Approx.), delete "N-methylpiperadinyl," and insert --N-methylpiperidinyl,--, therefor.

In Col. 19, Lines 28, 33, and 61; and Col. 20, Lines 1, 3, 6, 10, 14, 18, and 24, delete each occurrence of "or" and insert --or a--, therefor.

In Claim 3, Col. 19, Line 32, delete "aralkyl" and insert --alkaryl--, therefor.

In Claims 5, 6, and 8, delete each occurrence of "A compound" and insert --The compound --, therefor.

In Claim 6, Col. 19, Line 49, delete "benzyl." and insert --and benzyl.--, therefor.

In Claim 9, Col. 19, Line 67, delete "cycloalkyl," and insert --cycloalkyl and--, therefor.

In Claim 17, Col. 20, Line 29, delete "claim 1 or" and insert --claim 1, or a--, therefor.

In Claim 19, Col. 21, the chemical structure should read,

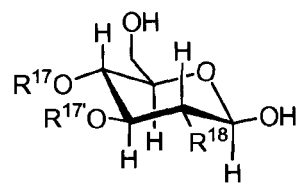

In Claim 19, Col. 22, Line 2, delete "are" and insert --are as--, therefor.